United States Patent
Hintsche

(10) Patent No.: US 7,367,221 B2
(45) Date of Patent: May 6, 2008

(54) SENSOR FOR DETECTION OF LIQUID INGREDIENTS, PARTICULARLY FOR BIOLOGICAL MATERIALS AND THE DETECTION DEVICE CONTAINED IN THE SENSOR

(75) Inventor: Rainer Hintsche, Berlin (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 225 days.

(21) Appl. No.: 11/119,298

(22) Filed: Apr. 28, 2005

(65) Prior Publication Data

US 2005/0268701 A1    Dec. 8, 2005

(30) Foreign Application Priority Data

Apr. 28, 2004  (DE) ............... 10 2004 020 829

(51) Int. Cl.
*G01N 11/00* (2006.01)
*G01N 27/403* (2006.01)

(52) U.S. Cl. .............. 73/53.01; 73/61.41; 422/58; 422/82.02; 422/98

(58) Field of Classification Search .......... 73/53.01, 73/61.41; 422/58, 82.01, 82.02, 98
See application file for complete search history.

(56) References Cited

U.S. PATENT DOCUMENTS

| | | | |
|---|---|---|---|
| 5,096,669 A | 3/1992 | Lauks et al. | |
| 2004/0038420 A1 | 2/2004 | Gelbart et al. | |
| 2005/0031490 A1* | 2/2005 | Gumbrecht et al. | ........ 422/63 |

FOREIGN PATENT DOCUMENTS

| | | |
|---|---|---|
| DE | 101 11 457 A | 9/2002 |
| DE | 101 11 458 A1 | 9/2002 |
| WO | WO 98/24544 A1 | 6/1998 |
| WO | WO 00/62047 | * 10/2000 |

* cited by examiner

*Primary Examiner*—Daniel S. Larkin
(74) *Attorney, Agent, or Firm*—Duane Morris LLP

(57) ABSTRACT

This invention relates to a sensor for the detection of liquid ingredients with a carrier element (10), a sensor element (1) on the carrier element (10) and a sensor array, which is disposed on the surface of the sensor element and contains one or more electrodes (2), which are in electrical contact (4) with the corresponding deflection surfaces (3), which are also on the surface of the sensor element (1), but otherwise not electrically connected to the carrier element (10). The sensor forms a detection unit together with a detachable cover, which has at least one fluid channel (7) for the feed line, as well as at least one contacting element (5) and which forms together with the sensor at least one hollow space (8) above the surface of the sensor element (1), where there is the surface or part of a surface of at least one electrode (2), but no deflection surface (3), while each contacting element is in such a manner disposed, that it contacts a corresponding deflection surface when the sensor connects with the cover. In specific embodiments, the sensor itself comprises in addition a covering element (6) firmly attached to the sensor, which constitutes at least one filling opening (12) and at least one hollow space (8) above a sensor element's surface (1), where there is the surface or part of a surface of at least one electrode (2), but no deflection surface (3). When connecting this sensor to a contacting element (5), it forms a detection unit, whereby each contacting element is in such a manner disposed, that it can connect to a corresponding deflection surface (3) of the sensor.

33 Claims, 2 Drawing Sheets

Figure 1:
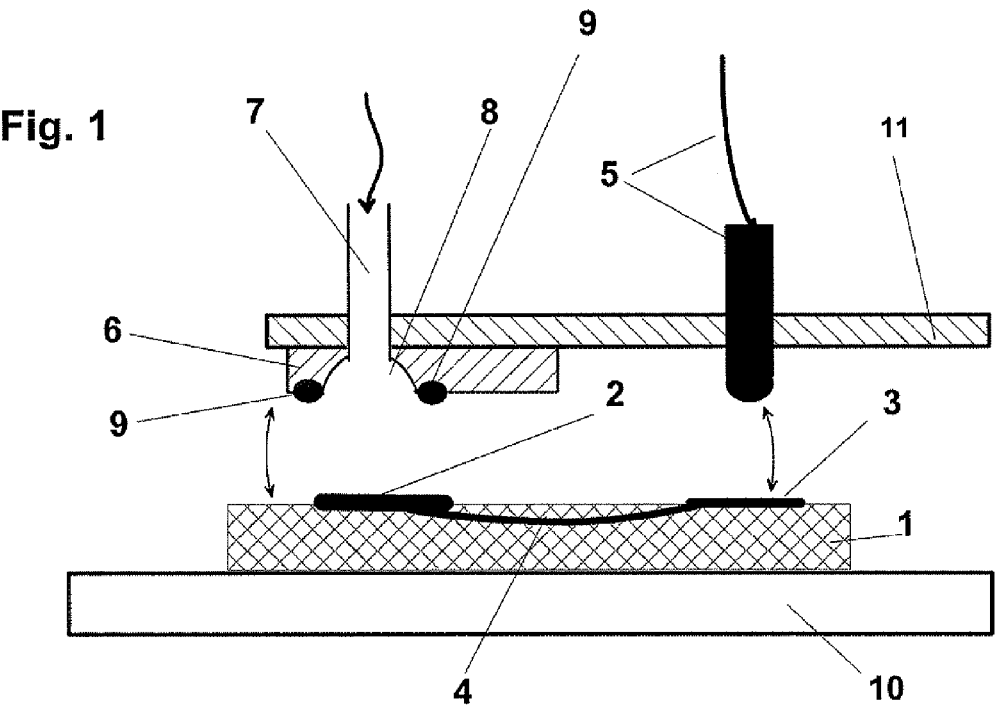

SENSOR FOR DETECTION OF LIQUID INGREDIENTS, PARTICULARLY FOR BIOLOGICAL MATERIALS AND THE DETECTION DEVICE CONTAINED IN THE SENSOR

This invention refers to a sensor with an electrochemical sensor array, particularly in the form of an electrode area and to a device for the chemical or biological analysis. The sensor is to be used together with contact elements and appropriate fluidic connections as a detection unit, which together with the detection device can detect electrochemical components of analysis liquids. This sensor is much more cost-efficient than other known sensors of the same kind. Both the electrical and the fluidic connections can be very easily established and detached, so that the sensor can be used as an exchangeable one-way element in diagnostic analyses apparatuses. It is also very easy to handle.

During the last 20 years, the micro system technology and micro sensor technology have developed an abundance of bio-chemical chip sensors, which has led to a considerable improvement in the miniaturized chemical analysis. Worth mentioning are the chip sensors based on optical and electrochemical principles, which are realized with the same technology as the semiconductor. The use of portable units for chemical and biochemical analysis with such one-way sensors requires a flexible exchange of sensor elements and corresponding reagents, if applicable. In doing so, the optical systems have already passed successfully through the technical implementation and introduction to the market; however most of the electrical systems have not yet gone beyond the laboratory prototype level. While optical-chemical or optical-biochemical sensor systems and optical bio-chips can be read out contactless with light beams, for the electrochemical based chip system, the required electrical connection to the corresponding gauges and the fluidic connection for the feeding of samples and liquids, respectively reagents, must be realized concurrently.

With the insertion of planar electrochemical sensors, like electrochemical sensors and field effect transistors in the silicon technology or even electrochemical sensors on polymer carriers or on those made of glass, an eventually required exchange requires the concurrent realization, respectively detachment of such electrical and fluidic contacts. The electrical connection is usually implemented through expensive contacting through bond wiring from the electrical deflection surfaces of the sensors or chips to the circuit paths through conventional conductor boards, respectively to the circuit paths through special carriers like glass or polymers. The U.S. Pat. No. 5,096,669 informs us of a system, wherein strip-shaped electrical contacts on the edges of several electrochemical planar sensors are used as wrap connections for the reversible creation of electrical deflections. The disadvantages of this system is the necessity to array electrical connectors on the edge of a small planar silicon sensor, the mechanical instability of edges of the Si-chip and an unfavorable position of the chips on the edges of the carrier system. The required fluidic sample feed occurs in this system through a discharge flow-through, which is directed over the active sensor area of the chips, so that large parts of the precious chip surface must be used for the durable sealing and have no ulterior usage.

Another system is revealed in the patent application, submitted by Siemens, DE 101 11 457 A1, regarding a diagnostic device. Here a sensor or chip is embedded in a substrate, through which one or more discharge flow lines are running and that are open on the substrate surface, such that the fluid flows along under the sensor. Whereas the substrate that is harboring the chip and the fluidic conductors is called applicator. The fluidic connection is for instance realized through the sealing application of a cover that also has fluidic channels, which fit exactly with the feed and draining in the applicator. The top is part of the readout unit.

The required electrical wiring and packaging of the sensor is described in detail in the patent DE 10 111 458 A1 of the same applicant, which shows a module of a diagnostic device. The conceptual formulation of this invention application is to avoid the waste of an active sensor surface, as is the case with the device described in U.S. Pat. No. 5,096,669, and to allow the manufacture of cost-effective products. This is achievable particularly because the case concept is to be geared as much as possible to the classic microelectronics. Accordingly, the sensors will be manufactured as chip-module with electrical wiring to a carrier in the wiring bond technology. However, the disadvantages of this typical semiconductor technology are the expensive circuit boards and costly bond technologies. The unstable bond wirings frequently have to be stabilized with a so-called sealing with hardenable polymer.

The chip sensors with fluid systems and guard contacts in diagnostic modules of the company Nanogen, San Diego, USA (see also application US 2004/038420 A1 and WO 98/24544 A1) show a similar construction. Here the guard contacts are connected to all sides of an electrical sensor chip with bond wiring, while the chip's electrodes are arranged in a flow-through chamber. The disadvantage of this device is the high manufacturing costs.

The previously mentioned DE 101 11 458 A1 contains a proposal already described in FIG. 6, which deviates from the other embodiments described there, in that neither the fluid lines nor the electrical connections run through the substrate that holds the chip or the sensor. Instead, a flow-through chamber is formed, when the top is placed on the substrate that contains the sensor, and thus a chamber is formed above the sensor. In- and outgoing fluid lines in the top part allow the fluid flow-through in the chamber, which is located lateral near the chip and is sealed with O-ring seal to prevent leakage. There is an electrical deflection here too, from the chip to the carrier, namely lateral near the chip. The chip is located on a carrier in the board's body and is fitted there with classical tools of the flip-chip-technology. Such tools are a PI-ring, an underfill and a so-called bump. The electrical deflection from the chip occurs through conductive components, which are led between the bump and an insulation, located across the sealant of the top part, and then to the top surface of the substrate, while they overlie on carrier material and are supported by additional components. There they touch the so-called contacting points of the top part, which are provided with attachable elastic electrical contacts. This embodiment is actually very cost-effective for the manufacturing of the substrate; however it requires complex components and procedures to accomplish the firmly installed electrical deflection from the sensor or chip to the contacting points.

The chemical-biochemical analysis systems with electrochemical sensors that were proposed so far, based on the above mentioned structures can be accomplished only in few numbers for the Si-technology and at relatively high costs. They are usually too expensive to be used as single analysis components or even as one-way material.

This invention's assignment is to provide an electrochemical sensor for the detection of liquid ingredients, which is far more cost-efficient to manufacture than other sensors until now. Its electrical feed and guard contacts should be easily detachable, so that it's easy to operate and if necessary also to use as single use component in an analysis system. Furthermore, it's this invention's assignment to provide a detection unit, which is structured in such a manner, that it can detect the liquid ingredients electrochemically together with the sensor.

The assignment is done by providing a sensor, which can detect liquid ingredients with the help of an electrode-sensor array that contain a carrier element and a planar sensor element on top of the carrier, on which lies the sensor array. The sensor array's electrodes are also connected to the deflection areas on the surface of the sensor element, through electric conductive connections, but other than that without electrical connection to the carrier element. The sensor element can be manufactured in usual silicon or glass technology. If applicable, plastics can also be carriers of metallic thin-film for electrodes, connections and deflection surfaces and as such be used as materials for the sensor element. The use of a silicon chip is very convenient. The carrier element is a cheap, unstructured and contactless carrier.

Thin, electric conductive metallic layers form on the sensor element both the electrode and the deflection surfaces. They can be manufactured with the thin layer technology, for example inserted in the chip surface or through sputtering or vacuum moralized. The electric conductive connections or contacts can also be manufactured with this technology. In doing so, all three parts required for the electrical part can be integrally manufactured. Then they usually are located on a horizontal layer.

The electric connection between the electrode and the deflection surface can remain open on the surface of the sensor element. It is however advantageous to isolate it from the surface of the sensor element. This can for instance occur through the application of an inorganic, inorganic-organic or organic insulating material, for example silicon oxide or a silicon oxynitride or a plastic, like lacquer. Instead, the electric conductive connection between the electrode and the deflection surfaces can be manufactured with the usual semiconductor technology, for instance through CMOS-circuits. In doing so, the electric connection from the electrodes into the silicon material occurs through an insulating interface layer to the usual chip structures, like for instance transistor circuits in the CMOS-technology, which for example can act as active measuring circuits for each array electrode. From these integrated structures we establish an electric duct towards the surface to the deflection surfaces. The fluidic and electrical connection is therewith identical for both sensor types.

For example in exemplary embodiments, when classical Si-thin-film technology is used for the manufacturing, the sensor element can have dimensions from 3×3 mm to 10×10 mm. From here we usually use approximately 1×3 mm for the electrode array. The form of the metallic deflection surfaces is arbitrary; they can be circular or rectangular. Its dimensions are usually around $0.1$ $mm^2$ to $2$ $mm^2$, preferably up to $1$ $mm^2$. However we must emphasize, that these are only examples; the size of the sensor and its components can be freely chosen according to its application and usage.

The number of existing electrodes in the sensor array can be freely chosen according to its usage. It is convenient to provide similar electrodes, in order to conduct several analyses (whether for the detection of various substances or for the analysis of various samples of the same substance) at the same time, respectively in parallel. The trigatron electrodes used for the electrochemical sensors, like for instance backplate electrodes and/or reference electrodes, can also be disposed on the sensors.

The sensor can be combined with a cover; together they form a detection unit, which in connection with an analysis apparatus, can act as detection unit and detect liquid ingredients, particularly those of biological origin.

The cover is shaped in such a way, that together with the sensor it forms one or more hollow spaces above the surface of the sensor element, where we find the surface or part of a surface of one or more electrodes (the latter for instance for the analysis of several ingredients in a fluid). At least one fluidic line in the cover creates a fluid connection from at least one of the hollow spaces through the cover. This fluid line can be connected with devices for feeding and suction of fluids in the respective hollow space, or can be locked with a septum, which is punctured with a hollow needle, to feed or drain liquid. Alternatively, there can be two liquid connections per each hollow cavity, where one acts as feeding line, the other as discharge line. The sensor can then be used together with the cover as a flow-through measuring cell.

Alternatively or additionally, we can also build a bigger hollow space in the cover, to be used as a collecting container for measuring and/or sample liquids, and it can be provided with outward venting opening if necessary.

In another formation, we can also dispose hollow spaces and channels in the sensor carrier, with connection to the hollow spaces and/or channels in the cover.

The sensor itself is usually provided only with the electrode array (sensor array) for the contact with the liquid. The electrical connection between the electrode and the deflection surfaces should be kept clear. This is why either the sensor and/or the cover are preferably provided with sealing elements. Particularly when the sensor is a one-way material, but the cover can be used several times, it is preferale to keep the sensor clear from all other components, which are not necessarily required and to integrate these in the cover if applicable. Thus it is preferable to affix the sealing elements on the cover, for example O-rings or sealing foil. It is also possible, but not necessarily required, to configure the hollow space and the sealing elements in such a manner, that the liquid touches only the surface of the electrode, but not other sensor element surfaces. The sealing elements are then preferably placed in the border area of the electrode surfaces, or very close to it.

The cover further comprises electrical contact elements to establish detachable electric connections, which are mechanically attached to the deflection surfaces of the sensor. The electrodes on the surface of the sensor element can be sensed from outside through the electric contact elements. The number of contact elements usually corresponds to the number of deflection surfaces and therewith to the electrodes.

The cover should be shaped, so that its connection to the sensor can be easily detached. For this purpose it can contain a retractable device, a lever device or a clicking device, which will connect and disconnect it from the sensor. It can be connected to the carrier, or be an integral component of the carrier. Alternatively, it will be kept on the sensor exclusively through compressive forces.

The electric contact elements can simply consist of a metal pin, which is mechanically pressed onto the contact surface and can be removed anytime. Thus, the usual fixed contact, like the bonding of metallic deflection surfaces on the chips to conductor paths on chip carriers, respectively substrates, is redundant. It is also advantageous to use spring born pin contacts as contact element, available in different embodiments, with diameters from 0.8 mm. Simple spring contacts can also be used, like the ones used in miniature connectors, for direct electric contact.

A special embodiment of this invention uses foil-like electric conductive plastics or even elastic plastics with metallic conductive structures as reversible micro contacts.

In all these cases, the contact elements can be kept together or in groups by an insulating fastener.

The electric contact elements, or a part or a group of them, can be disposed together with the fluid channels of the removable cover in a common mechanical fastener.

An alternative basic design of this invention is a covering element, which is already a sensor component and is firmly connected to it. Together with the corresponding surface it forms a hollow space, where there is a surface or partial surface of at least one electrode, but no deflection surface. The hollow space communicates with a filling opening for liquids. The same applies to the number and disposition of the hollow space(s) and of the electrode array lying below, for the hollow space(s) from the sensor and removable cover as mentioned above. Comparatively we can also provide an additional liquid drain in the cover, in order to operate the combination of sensor and firmly attached covering elements as a flow-through cell.

The covering element is fixed on the carrier element and/or sensor element, for instance with adhesive joints or heat sealing or elastic sealing. This mounting allows the hollow space above the electrode to be sealed against the rest of the sensor surface, and the electrical deflection surfaces are protected from short-circuiting. The covering element features a recess in the region of the deflection surface(s), so that the deflection surfaces can be reached from the top.

The disadvantage of this embodiment is the higher manufacturing cost for this sensor, as an additional part has to be manufactured through injection molding and mounted. However, it has certain advantages. The covering element can contain structures which lower the required work steps for detection and the standardized measuring solution and/or the fresh preparation of less stable solutions is no longer necessary. Thus we can provide one, some, or all filling openings and the hollow space with a filling channel, which can feature reserve niches for the absorption of reserve reagents.

The reserve reagents can be liquid. Alternatively, they can be solid and dissolve during the filling process and be transported in the hollow space above the electrode. Here chemical and biochemical reactions can take place that are necessary for the analytical process, like for instance a biochemical assay. Filling openings, filling channels and hollow spaces are provided at your option for liquid and/or solid reagents in the cover.

The supply of similar sensors with different reagents in the one-way element allows the cost-effective realization of various target substances, like the ones required in the biochemical analysis with its large number of molecular alternatives and affinity bonds.

The hollow spaces can typically have a volume between 1-100 µl, whereas the filling channels usually have a diameter of 0.1-0.5 mm. The sample's volume and liquid portions based on these dimensions are typically 1-500 µl. All other dimensions correspond to the values given for the combination of sensor and detachable cover described above.

If the reserve reagents are liquid, we can use gases for their transportation. Alternatively, we can provide the cover above the hollow space(s) with an elastic membrane, which can be used for the hydraulic transportation of the liquids from the reserve niches. If the reserve reagents are solid, they can be dissolved during the filling of the channels. The already mentioned alternative basic design with liquid drain for the hollow space above one or more or all electrodes, respectively parts of electrodes, but if necessary also for other additional hollow spaces, respectively channels, is particularly convenient for such cases in order to simplify the reaction, rinsing and measuring.

If we insert a sensor according to the alternative embodiment of this invention, the only compulsory required additional element for the entire detection unit is an electrical contact element for each deflection surface of the sensor, which can be mechanically attached to it. The liquid feed and drain must not be placed in the same element that contains this/these contact element(s). However, it is possible to provide a carrier for this, which also features the appropriate number of flow-through channels required for the supply of the hollow space(s) formed in the measuring cell(s). These flow-through channels are preferably provided with sealing elements, in order to ensure a detachable, but sealed connection between the flow-through channel and filling opening when the parts are compressed. Alternatively, they can be shaped as a hose, which can be inserted in the filling opening of the cover or inverted.

This invention's embodiment can also contain the above-mentioned optional features, for instance one or more fasteners for the electrical contact elements and/or flow-through channel(s), the addition of a retractable device, a lever device or clicking device or the like.

The enclosed figures display exemplified embodiments of this invention, whereas

Figure 2:
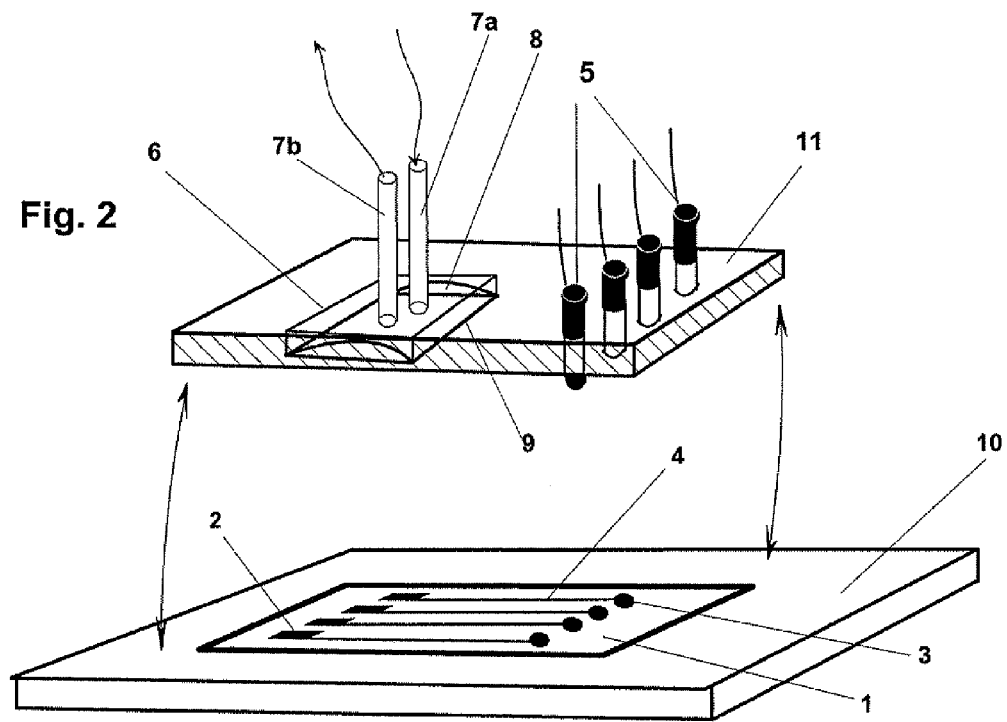
Figure 3:
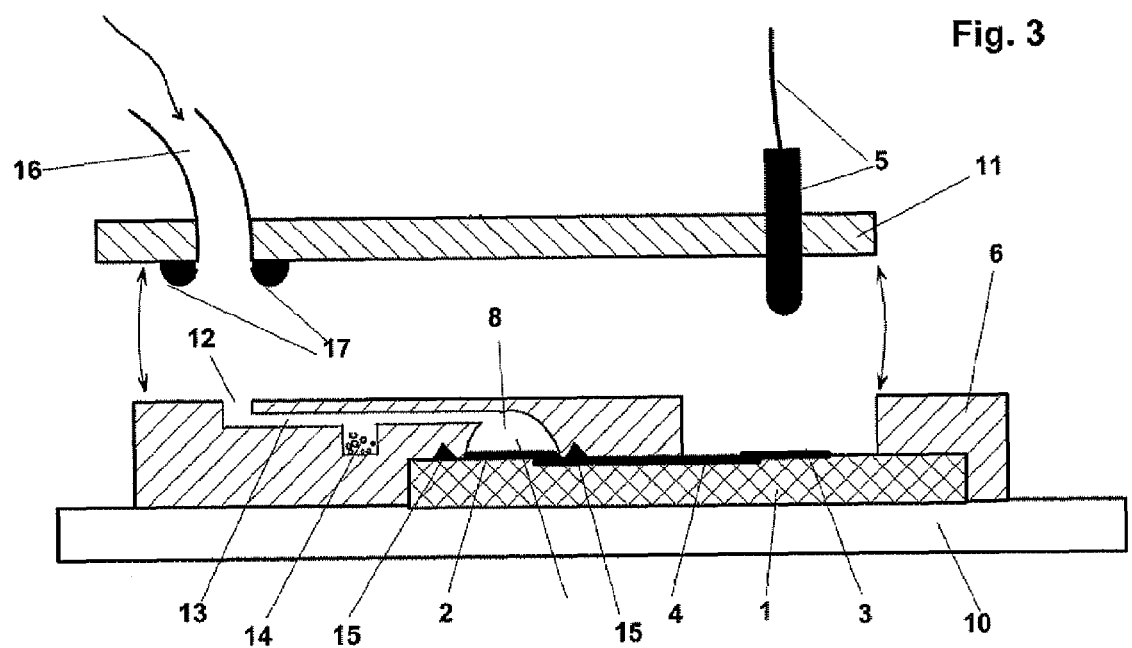

FIG. 1: displays the section through a sensor array with mechanical element for the realization of detachable electrical contacts combined with a detachable cover to allow the filling with liquids, FIG. 2: displays the top view of a sensor array on a carrier element and the associated mechanical element for the concomitant realization of electrical contacts near the cover for the filling with liquids, FIG. 3: displays a section through a sensor array with a fixed attached cover and the associated mechanical element for the concomitant realization of electrical contacts near the filling with liquids.

With the combination of a sensor and cover, according to this invention, we can create a system, which allows the quick exchange of the electrochemical sensor arrays used as one-way elements, particularly required in the biochemical analysis. By creating detachable electrical connections directly on the sensor element, the fixed attached electrical connections between the sensor element and the carrier, which have been required up to now, like those known from Si-chips on circuit boards or other circuit paths in the form of bond connections, can be omitted and thus save considerable technological costs, while at the same time, the realization of the feeding and draining lines to and from the electrodes is very easy. According to this invention, it is possible to create a sensor element with simple thin-film-chip technique, which makes its use much simpler and with more cost-efficient materials (e.g. glass, ceramics, plastics, paper, cardboard, circuit boards, carriers with flexible texture, etc.), besides the extreme adequate Si-chip, instead of the expensive circuit boards used so far or circuit paths on the so-called flextape or cheque-card technology.

The problem with all electrochemical sensor elements is the realization of liquid transportation for the supply of samples concomitant in close proximity of electrical contacts and on a comparable small Si-chip. A solution for both problems, according to this invention, is to provide sealed covers over the active parts of the sensor array combined with a reversible electric contact directly on the sensor surface.

The invention shows the creation of a hollow space above the electrochemical active chip elements and the electrochemical sensors through the cover, which acts as a measuring cell. By using the sealing in the appropriate place, the liquid and sample supply is limited to the sensor elements only, while the chip's open electrical contact surfaces required for the contact are protected. This is possible either through a cover with sealing itself or an adhesive sealing of the cover and an additional element for the liquid supply, which was also provided with sealant. Through the recess of this cover it is possible to realize a direct electrical contact of the electrical deflection surfaces on the sensor array through mechanical elements.

Another advantageous application of this invention is the construction of additional hollow spaces in the cover, described above, which are connected through channels. These hollow spaces can be used for the absorption of solid and/or liquid reagents. One or more openings in the cover will be used for the liquid supply to dissolve reagents and transport them in the cover to the electrochemical sensor array and thus operate chemical or biochemical reactions. The openings can also be covered with a septum, which is punctured with a hollow needle for the insertion of liquids and samples.

Another advantageous application of this invention is the cover's use for the pneumatic transportation of liquids. For that purpose, built-up liquids and/or reagents in the cover are transported in the cover's hollow spaces system and channel system by means of gases in the filling opening.

Another advantageous application of this invention is the cover's use for the hydraulic transportation of liquids. For this purpose a larger hollow space in the closed cover will be covered with an elastic membrane. Through mechanical pressure of this membrane, the liquids and/or reagents built-up in this hollow space will be transported in the cover through appropriate channels, respectively hollow spaces. In doing so, the cover should be provided with openings for the pressure equalization in the fluidic system. In the embodiments with cover, the used liquids and liquids no longer required, for example after the washing and reaction steps, can be removed from the flow-through or deposited in the cover itself. The cover will contain special hollow spaces for this purpose, and it will be used as a waste reservoir, which can be filled through the channels.

This invention solves the problem of reversible electric contacts without bonding. Through various kinds of needle contacts and spring contacts, like the ones commonly used for checking purposes in the semiconductor technology, the deflection surfaces can be contacted on the chip directly and reversibly. The positions and dimension of these deflection surfaces on the chip and their distance from the cover containing the liquids can be adjusted through the chip's design. The contacts will be used individually or in groups, according to the arrays, and are isolated mechanically joined to each other.

The combination of fluidic and electric chip connection according to this invention allows a simple exchange of electrochemical sensor arrays and makes it possible for them to be used as one-way sensors, also called disposables.

More details and advantages of this invention result from the subsequent description of embodiment examples with the enclosed figures.

FIG. 1 illustrates schematically a sensor array with a mechanical element for the realization of removable electric connections in a detachable cover to be filled with liquid. The sensor array consists of the actual planar sensor chip 1 in Si-chip technology or glass technology with thin-film electrodes 2 as electrochemical sensors on the surface, as well as metallic deflection surfaces 3 also in thin layer technology, while 2 and 3 are connected to each other through an electric conductive connection 4.

Item number 5 describes a mechanically mobile, electric contact element for the realization of removable electrical connections. According to this invention the combination of this removable electric contact on the chip itself with the concurrent connection of fluidic elements is important. The fluidic connection to the electrodes 2, acting as sensor elements, is accomplished in this embodiment through the cover 6, which is connected with the hollow space 8 through a filling channel 7.

The protection of the electric contacts from liquids occurs through the pressing of the sealing element 9 on the chip. The sealing element 9 can for instance be an O-ring or a sealing foil.

The mechanical electrical contact element 5 is mechanically connected to the fluidic element, which consists of parts 6-9, through a carrier 11. The carrier 11 can be part of a simple retractable device, lever device or clicking device. The connection of the electric and fluidic contact and the simple solubility from the sensor array allows the operating-friendly exchange of the one-way chip. The cost-efficient application according to this invention requires only a cheap carrier as one-way part, like for instance a polymer carrier with a glued on Si-chip. The expensive circuit boards used so far and expensive bonding processes for the electrical chip contacting can be omitted. This is very advantageous for the Si-chips with cheap thin-film technology, where even an enlargement of the required chip surface for the adaptation to the proposed solution constitutes only a fraction of the saved costs for material and assembly.

FIG. 2 illustrates the top view of the sensor array 1 in Si or glass technology with several thin-film electrodes 2, with several metallic deflection surfaces 3 and the associated electric conductive connections 4 on a chip carrier 10. The chip carrier 10 is advantageously manufactured from polymers, organic plastics, glass or even cardboard and it requires no special structures or provisions. The mechanical contacting elements 5 which correspond to the arrangement of the deflection surfaces, in this case serve for the connection and disconnection of several parallel electric connections. They are fastened isolated in the carrier 11, which is for instance made of polymer or metal. Under the carrier 11 is the cover 6, which shows a recess 8 for the creation of the hollow space. The corresponding hollow space 8 is pressed against the sensor array 1 with the sealing 9, which again can be a simple O-ring. The liquid supply to the hollow space 8 occurs through the filling channel 7a. The liquid can be drained through the filling channel 7b and thus the function of a conventional flow-through cell is created.

The hollow spaces have typical volumes between 1-100 μl, while the filling channels, which can be made of small steel pipes and fastened in the carrier 11, usually have a diameter between 0.1-1 mm. The sample's volume and liquid portions based on these dimensions are typically 1-500 μl.

Another embodiment is illustrated in FIG. 3 as a section. A sensor array 1, which is made as in FIGS. 1 and 2, is fastened to the chip carrier 10, for instance through adhesive joining. In addition, the cover 6 is also fastened to the chip carrier 10 through adhesive joining 15. Here, the filling of the hollow space 8 is realized through the electrode 2 with liquids through the filling opening 12 and a filling channel 13. Along the filling channel 12 there is a hollow space 14, which contains solid or liquid reagents. The solid reagents are dissolved during the filling process and transported in the hollow space through the electrode. Here, chemical and biochemical reactions; can take place that are necessary for the analytical process, like for instance a biochemical assay. Optionally, several filling openings 12, filling lines 13 and hollow spaces with solid reagents 14 in the cover can be provided. The filling element 16 is provided for the filling and realization of a removable fluidic connection, which is pressed with the sealing 17 towards the filling openings 12. The filling element 16 can be a hose or a small metallic pipe.

The realization of removable electric connections is accomplished through analogous mechanical elements 5, which are comparable to those in FIG. 1 and FIG. 2. In this embodiment, it is important that openings in the cover 6 remain recessed, which allow the unobstructed access of the mechanical elements 5 to the metallic deflection surfaces 3 on the sensor array 1.

The hollow spaces have typical volumes between 1-100 µl, whereas the filling channels have a usual diameter of 0.1-0.5 mm. The sample's volume and liquid portions based on these dimensions are typically 1-500 µl large. The rest of the materials and dimensions correspond to the values specified for FIGS. 1 and 2.

According to this invention, for this embodiment, the concomitant and combined connection of filling elements and the realization of a removable electric connection are thereby realized, that the filling element 16 and the contact element 5 for the realization of removable electric connection are mechanically fastened to each other. For this purpose, the carrier 11 can be shaped for instance as a valvular lid or lever device.

Thus we created a device, which allows the cost-efficient realization and simple operation of electrochemical sensor arrays as one-way items in the chemical and biochemical analysis. Thus, the particularly decentralized application of these sensors and their implementation in the on site analysis can be accomplished even with less trained operating personnel.

The invention claimed is:

1. Sensor for the detection of liquid ingredients, comprising:
    a carrier element,
    a sensor element on the carrier element, and
    a sensor array, which is disposed on the sensor element's surface and contains one or several electrodes, which are in electrical contact with associated deflection surfaces, which are also located on the surface of the sensor element, but otherwise not in electrical connection with the carrier element.

2. Sensor according to claim 1, wherein the sensor element is made of silicon or glass or plastic.

3. Sensor according to claim 1 wherein electrical contacts are realized between the electrodes and the deflection surfaces in the same horizontal layer as those on the surface of the element.

4. Sensor according to claim 1 wherein the electrodes and the deflection surfaces are placed in the surface of the sensor element or separated as a thin metallic layer on top of it.

5. Sensor according to claim 4, wherein electrical contacts between the electrodes and the deflection surfaces are also located in the sensor element's surface, or are deposited as a thin metallic layer on top of it, so that the electrodes, the deflection surfaces and the electrical contacts are manufactured together or consecutive and integral.

6. Sensor according to claim 1 wherein electrical contacts between the electrodes and the deflection surfaces are covered by an insulating material from the surface of the sensor element.

7. Sensor according to claim 6, wherein the insulating material is present as a thin layer on the electrical contacts.

8. Sensor according to claim 6, wherein the insulating material from the surface of the sensor element is an inorganic oxide, a nitride, an oxynitride, or an organic or inorganic-organic plastic.

9. Sensor according to claim 8, wherein the inorganic oxide is $SiO_2$.

10. Sensor according to claim 8, wherein the oxynitride is silicon-oxynitride.

11. Sensor according to claim 1, wherein electrical contacts are embedded as integrated circuits in the sensor element.

12. Sensor according to claim 1, further comprising:
    a covering element firmly attached to the sensor, which constitutes at least one filling opening and at least one hollow space above the sensor element's surface, wherein there is a surface or part of a surface of at least one electrode exposed, but no deflection surface.

13. Sensor according to claim 12, wherein the hollow space is sealed from other parts of the sensor through sealing elements.

14. Sensor according to claim 12, wherein the covering element is fastened to the carrier element and/or to the sensor element, particularly with adhesive joints, and includes a recess in the area of the deflection surfaces, so that the deflection surfaces are exposed.

15. Sensor according to claim 12, wherein each filling opening is connected to the hollow space through a fluid line, while one, or each fluid line is optionally equipped with one or more supply niches for the absorption of supply reagents.

16. Sensor according to claim 12, wherein the covering element has at least one feeding channel and at least one draining channel.

17. Detection unit for the detection of liquid ingredients, comprising a sensor according to claim 1, and further comprising:
    a detachable cover, which has at least one fluid channel for feeding purposes, as well as at least one contacting element and when connecting the sensor with the cover, the cover builds with the sensor at least one hollow space above the surface of the sensor element, where there is the surface or part of a surface of at least one electrode exposed, but no deflection surface, while each contacting element is in such a manner disposed, that it contacts a corresponding deflection surface when the sensor connects with the cover.

18. Detection unit according to claim 17, wherein the contacting elements are pin contacts or spring contacts or that the contacting elements are built as fixed contacts.

19. Detection unit according to claim 17, wherein the cover has at least one feeding channel and at least one discharge channel.

20. Detection unit according to claim 17 wherein either the sensor and/or the cover contain at least one sealing element, which ensures, optionally together with other sealing elements a liquid-tight sealing of the hollow space.

21. Detection unit according to claim 20, wherein the sealing element is an O-ring or a sealing foil.

22. Detection unit according to claim 17, wherein the cover contains a carrier, through which one or more fluid channels pass.

23. Detection unit according to claim 22 wherein the cover's carrier includes a recess, which is part of the hollow space.

24. Detection unit according to claim 17 wherein the cover contains a retractable device, a lever device or a clicking device, which connects the cover to the sensor and also separates the cover from the sensor.

25. Detection unit according to claim 24, wherein the retractable device, the lever device or the clicking device is connected to the carrier.

26. Detection unit according to claim 17 wherein the cover contains at least one covering element, through which pass one or more fluid channels and which includes a recess, while the contacting elements are disposed farther from the covering element.

27. Detection unit according to claim 17, wherein one or more fluid channels are closed with a septum, which can be punctured with a hollow needle.

28. Detection unit for the detection of liquid ingredients, comprising a sensor according to claim 12, and further comprising
at least one contacting element, whereby each contacting element is disposed in such a manner that it can connect to a corresponding deflection surface of the sensor.

29. Detection unit according to claim 28, wherein the contacting elements are fastened to a carrier, which includes at least one flow-through channel, to such an extent that, when connecting the sensor with the carrier each contacting element can come in connection with a corresponding deflection surface and each flow-through channel communicates with a fluid channel.

30. Detection unit according to claim 29, wherein each flow-through channel includes at least one sealing element at a bottom end, for a detachable sealing connection of the flow-through channel and fluid channel.

31. Detection unit according to claim 29, wherein the cover contains a retractable device, a lever device or a clicking device, which connects the cover to the sensor and also separates the cover from the sensor.

32. Detection unit according to claim 29 wherein one or more fluid channels are closed with a septum, which can be punctured with a hollow needle.

33. Detection unit according to claim 28, wherein the contacting elements are pin contacts or spring contacts or that the contacting elements are built as fixed contacts.

* * * * *